United States Patent [19]
Emery

[11] Patent Number: 5,608,516
[45] Date of Patent: Mar. 4, 1997

[54] GLASS BOTTLE INSPECTION MACHINE

[75] Inventor: Monti D. Emery, Elmira, N.Y.

[73] Assignee: Emhart Glass Machinery Investments Inc., Wilmington, Del.

[21] Appl. No.: 572,267

[22] Filed: Dec. 13, 1995

[51] Int. Cl.$^6$ .................................................. G01N 21/00
[52] U.S. Cl. ........................................ 356/240; 250/223 B
[58] Field of Search ........................... 356/196, 183, 356/240; 250/223; 209/111.7; 198/40, 160, 162, 165, 167, 76, 278, 283

[56] References Cited

U.S. PATENT DOCUMENTS

| | | | |
|---|---|---|---|
| 3,557,950 | 1/1971 | Powers | 209/111 |
| 3,811,553 | 5/1974 | Riggs | 198/283 |
| 3,848,742 | 11/1974 | Krenmayr | 209/111 |
| 3,991,883 | 11/1976 | Hobler | 209/73 |
| 4,252,230 | 2/1981 | Eriksson | 198/344 |
| 4,967,070 | 10/1990 | Ringlien et al. | 250/223 |
| 5,405,015 | 4/1995 | Bhatia et al. | 209/524 |
| 5,419,350 | 5/1995 | Wegner | 134/79 |

*Primary Examiner*—Frank Gonzalez
*Assistant Examiner*—Michael P. Stafira
*Attorney, Agent, or Firm*—Spencer T. Smith

[57] ABSTRACT

A machine for inspecting a glass bottle comprising a bottle supporting track, a car for conveying a bottle along the track to a bottle inspection station. The car includes rollers for rotatably engaging one side of the bottle and a wall mechanism forcefully engages the other side of the bottle as it is conveyed to the bottle inspection station. The wall mechanism includes a pivotally displaceable support, which is biased towards a fully advanced position. Linear bumpers secured to the support extend into the path of a conveyed bottle when the support is at the fully advanced position so that a bottle will engage the linear bumpers and forcefully pivotally displace the support to a retracted position as the bottle is conveyed to the inspection station. The length of the linear bumpers is selected so that when a bottle is conveyed to the inspection station, the bottle will be conveyed past the linear bumpers whereby the support will be displaced back to the fully advanced position. When this occurs, rotating drive rollers on the support forcefully engage and rotate a bottle at the inspection station. The rotating bottle is then inspected.

4 Claims, 3 Drawing Sheets

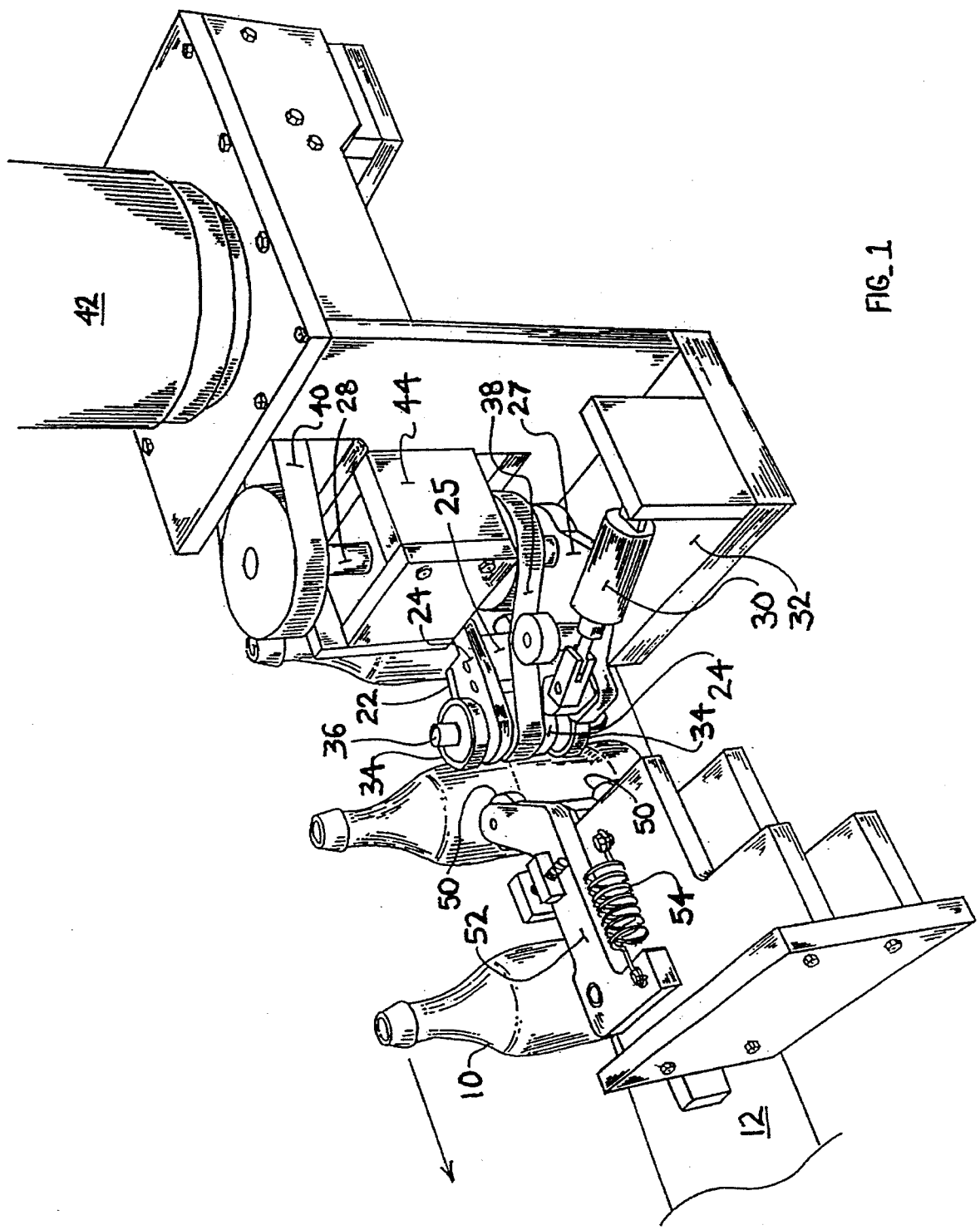
FIG_1

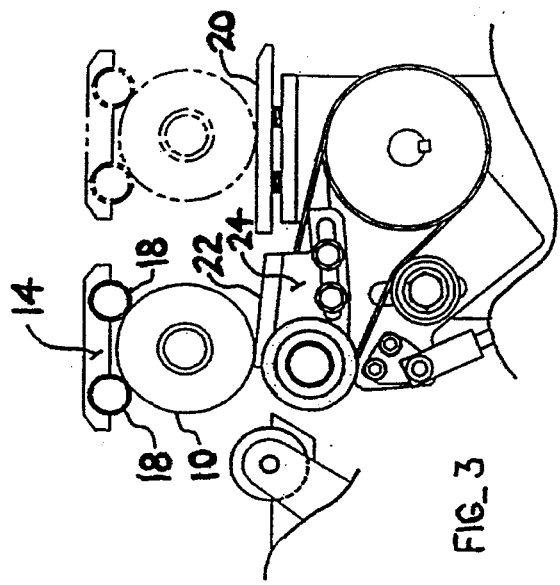
FIG_3
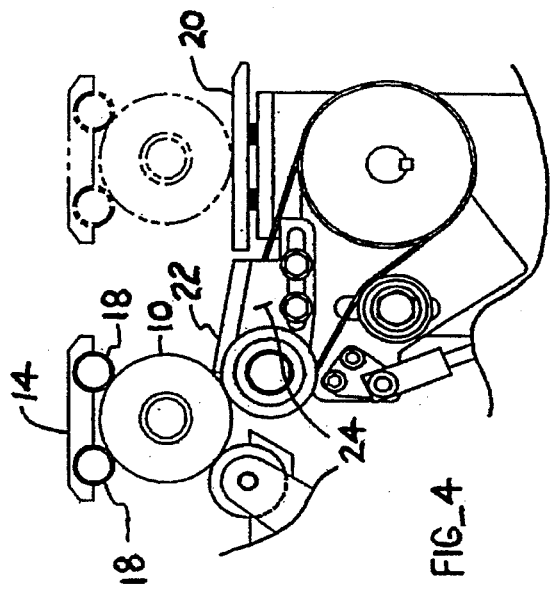
FIG_4
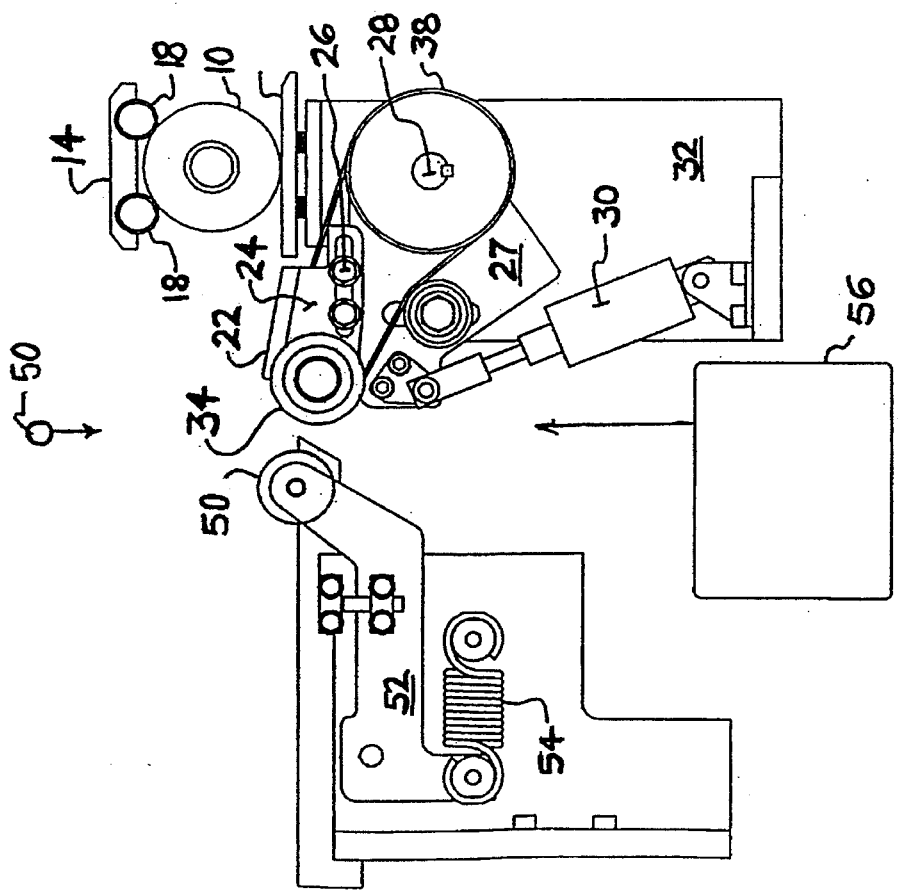
FIG_2

GLASS BOTTLE INSPECTION MACHINE

The present invention relates to machines for inspecting glass bottles and more particularly to such machines which stop and inspect a bottle while it rotates at an inspection station.

Bottle inspection, to keep up with the manufacturing process, should occur at the rate of at least 400 bottles per minute. At such a rate, bottle stability is a key concern and this problem is greatly magnified when bottle rotation at an inspection station is required.

Earlier designs for inspecting a bottle rotating at the inspection station can propel bottles from the inspection station and this is very undesirable.

It is accordingly an object of the present invention to provide an inspection machine which can rotate a stopped bottle at an inspection station without losing control of the bottle.

Other objects and advantages of the present invention will become apparent from the following portion of this specification and from the accompanying drawings which illustrate in accordance with the mandate of the patent statutes a presently preferred embodiment incorporating the principles of the invention.

Referring to the drawings:

FIG. 1 is an oblique view illustrating the inspection station of a machine for inspecting a glass container such as a bottle;

FIG. 2 is a stop view of the inspection station at the time when a conveyed bottle first engages a wall mechanism;

FIG. 3 is a view similar to that of FIG. 2 at the time when the conveyed bottle is located at the end of the elongated bumper on the wall mechanism;

FIG. 4 is a view similar to that of FIGS. 2 and 3 at the time when the conveyed bottle is stopped at the inspection station.

Figure 5:
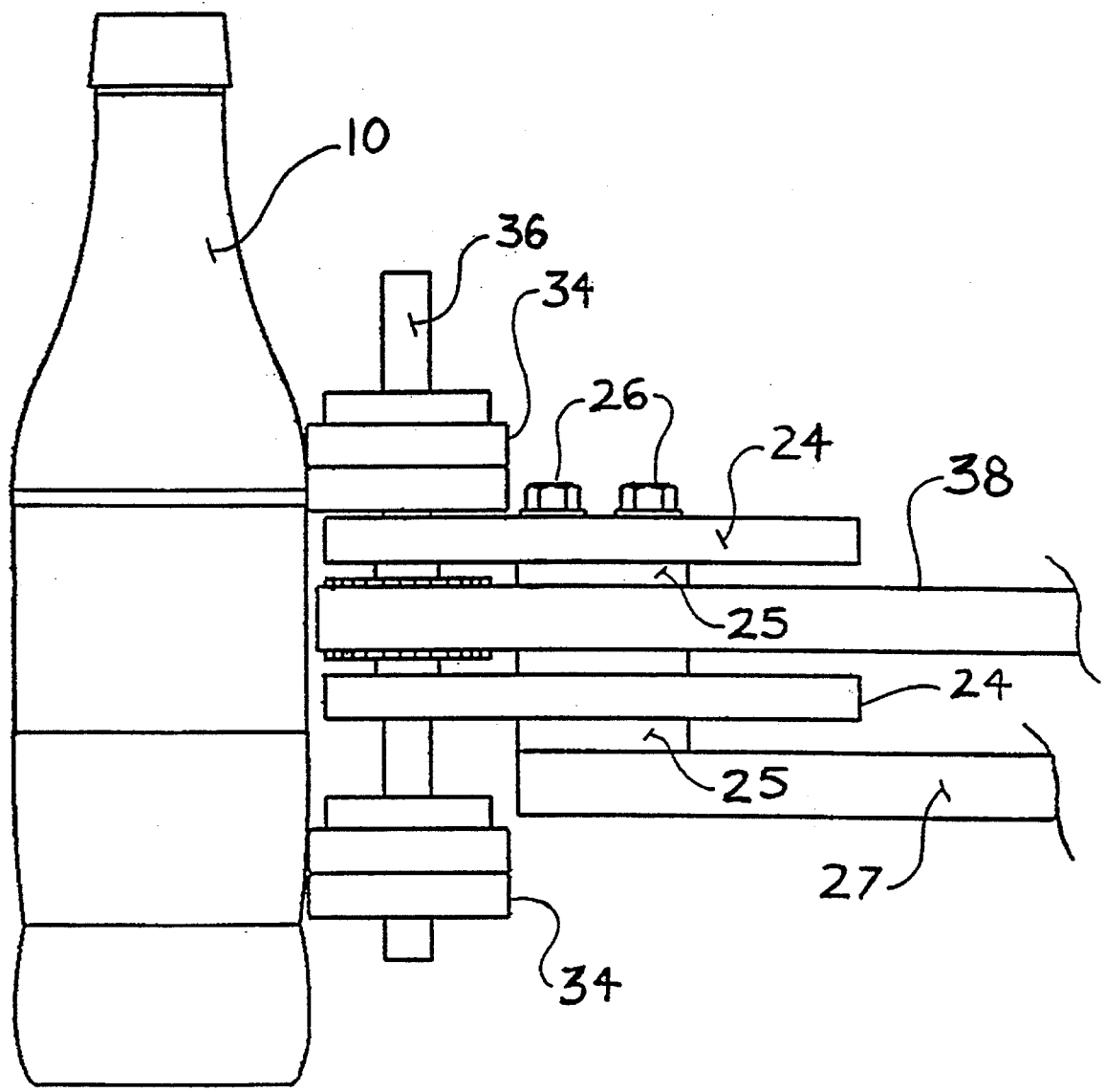
FIG. 5 is a side view of the pivotal wall mechanism of the inspection machine shown in FIG. 1.

Bottles 10 are carried by a conveyor 12 which defines a bottle path or track. As a bottle approaches the inspection station, a car 14 (FIGS. 2–4), which is part of a drive chain (not shown) and which is traveling at the same speed as the conveyor 12, captures a bottle between upper and lower spaced roller pairs 18. The bottle is now located between the spaced rollers 18 on one side and a wall 20 on the other (FIG. 2).

As the bottle approaches the inspection station (FIG. 3) upper and lower linear bumpers 22 (the upper linear bumper is partially cut away in FIG. 2 to show the lower linear bumper) which are strips of plastic, extend into its path. Each linear bumper is secured to a support 24 and the supports, with suitable spacers 25, are secured with screws 26 to a bracket 27. The bracket is secured to a spindle shaft 28 so that it can be normally pivotally displaced by an air cylinder 30, which extends between the bracket 27 and the housing 32, to locate the linear bumpers 22 at a fully advanced position (FIG. 2).

Further displacement of the bottle gradually pivots the bracket about the spindle shaft 28 to a fully retracted position shown in FIG. 3. When the bottle reaches the inspection station (FIG. 4), the bottle will be past the linear bumpers thereby allowing the linear bumpers to be biased by the air cylinder towards the fully advanced position. As this happens, a pair of vertically spaced rollers 34 secured to a drive shaft 36 supported by the linear bumper supports 24 are forcefully brought into engagement with the bottle. Preferably, as shown in FIG. 5, the vertically spaced rollers 34 may be bushing mounted rollers so that they can be adjusted vertically up and down the drive shaft 36.

The drive shaft 36 is driven by a drive pulley system 38 which interconnects the drive shaft 36 and the spindle shaft 28. A motor pulley system 40 interconnects the spindle of a suitable continuously running motor 42 with the spindle shaft 28 which is supported by a bushing block 44 secured to the housing 32. A pair of idler rollers 50 supported by pivotally mounted arms 52 are biased by a spring 54, into forceful engagement with the bottle at the inspection station. When inspection is complete continued movement of the car forces the bottle past the idler rollers which pivot out of the way.

As can be seen from FIG. 2 a vision system, which includes a camera 56, views a bottle at the inspection station between the vertically spaced drive 34 and idler 50 rollers so that the sidewall of the bottle can be inspected. The bottle is back-lighted by a suitable light source 58.

I claim:

1. A machine for inspecting a glass bottle comprising a bottle supporting track, car means for conveying a bottle along said track to a bottle inspection station, said car means including roller means for rollingly engaging one side of said bottle, a wall mechanism for engaging the other side of the bottle as it is conveyed to said bottle inspection station, said wall mechanism including a displaceable support, means for biasing said displaceable support towards a fully advanced position, linear bumper means on said support, said linear bumper means extending into the path of a conveyed bottle when said displaceable support is at said fully advanced position so that a bottle will engage said linear bumper means and forcefully displace said displaceable support to a retracted position as the bottle is conveyed to the bottle inspection station, the length of said linear bumper means being selected so that when a bottle is conveyed to the bottle inspection station, the bottle will be conveyed past said linear bumper means whereby said displaceable support will be displaced back towards said fully advanced position, and roller means on said displaceable support for forcefully engaging the upstream portion of the other side of a bottle at the bottle inspection station when said displaceable support is displaced towards said fully advanced position, idler roller means for engaging the downstream portion of the other side of a bottle located at the inspection station, means for supporting said idler roller means so that further conveying of a bottle from the inspection station will displace said idler roller means out of the way of the bottle, means for driving said roller means so that a bottle located between said car roller means, said idler roller means and said displaceable support roller means at the inspection station will be rotated, and means for inspecting a bottle rotating at said inspection station.

2. An inspection machine according to claim 1, wherein said means for driving said displaceable support roller means continuously operates.

3. An inspection machine according to claim 2, wherein said displaceable support roller means comprises a pair of vertically separated rollers releasably secured to a vertical shaft.

4. An inspection machine according to claim 3, wherein said linear bumper means comprises a pair of vertically spaced plastic strips.

* * * * *